United States Patent [19]

Teranishi et al.

[11] 4,344,945

[45] Aug. 17, 1982

[54] PIPERIDINE DERIVATIVES

[75] Inventors: Masayuki Teranishi; Hiroyuki Obase, both of Machida; Haruki Takai, Kawasaki, all of Japan; Kazuhiro Kubo, Berchem, Belgium; Yutaka Kasuya, Komukainishi, Japan

[73] Assignee: Kyowa Hakko Kogyo Co., Ltd., Tokyo, Japan

[21] Appl. No.: 241,727

[22] Filed: Mar. 9, 1981

[30] Foreign Application Priority Data

Mar. 10, 1980 [JP] Japan .................................. 55-29106
May 27, 1980 [JP] Japan .................................. 55-69619

[51] Int. Cl.$^3$ ................. C07D 413/04; A61K 31/445; A61K 31/535; C07D 498/14
[52] U.S. Cl. ........................... 424/248.52; 424/248.53; 424/248.54; 424/248.55; 424/248.57; 424/246; 544/92; 544/95; 544/11

[58] Field of Search ............... 544/92, 95; 424/248.52, 424/248.53, 248.54, 248.55, 248.57

[56] References Cited

U.S. PATENT DOCUMENTS

| | | | |
|---|---|---|---|
| 3,513,166 | 5/1970 | Richman | 544/92 |
| 3,542,774 | 11/1970 | Shavel et al. | 544/92 |
| 4,144,344 | 3/1979 | Eichenberger et al. | 424/267 |
| 4,148,796 | 4/1979 | Yamamoto et al. | 546/199 |
| 4,166,117 | 8/1979 | Vincent et al. | 424/251 |

FOREIGN PATENT DOCUMENTS 2507639 9/1975 Fed. Rep. of Germany .

*Primary Examiner*—John M. Ford
*Attorney, Agent, or Firm*—Craig and Antonelli

[57] ABSTRACT

New piperidine derivatives which have a useful pharmacological activity such as hypotensive activity are prepared.

7 Claims, No Drawings

PIPERIDINE DERIVATIVES

The present invention relates to novel piperidine derivatives, acid addition salts thereof and pharmaceutical compositions containing the same.

The piperidine derivatives are compounds represented by the formula [I]:

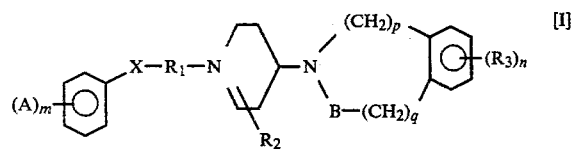

wherein A is hydroxy, halogen, lower alkyl, lower alkoxy, lower alkenyloxy, lower alkynyloxy, lower alkylthio, carboxy, lower alkoxycarbonyl, nitro, amino, lower alkylamino, lower alkanoylamino, sulfamoyl, mono- or di-lower alkylaminosulfonyl, lower alkylsulfonyl, carbamoyl, cyano or trifluoromethyl, m is 0 or an integer of 1–5, and when m is 2 or more, each A is the same group or each A is a different group or two A groups may combine to form lower alkylenedioxy; X is oxygen, sulfur, carbonyl, hydroxymethylene or methylene; $R_1$ is straight-chain alkylene having 1–4 carbon atoms with or without lower alkyl substitutent(s); $R_2$ is hydrogen or lower alkyl; p and q are 0 or 1 provided that p and q are not both 0 or 1 at the same time, B is

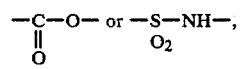

and when p is 1 and q is 0, B is

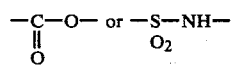

and when q is 1 and p is 0, B is

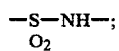

and $R_3$ is hydroxy, lower alkoxy, halogen, trifluoromethyl, trifluoromethoxy, trifluoromethylthio, nitro or amino, n is 0 or an integer of 1–4, and when n is 2 or more, each $R_3$ is the same group or each $R_3$ is a different group, or two $R_3$ groups may combine to form lower alkylenedioxy.

The compounds represented by the formula [I] and the pharmaceutically acceptable acid addition salts thereof have a hypotensive activity, and therefore are useful as medicine.

Heretofore, the following compounds, each having a piperidine ring, are commercially available as tranquilizers.

benperidol

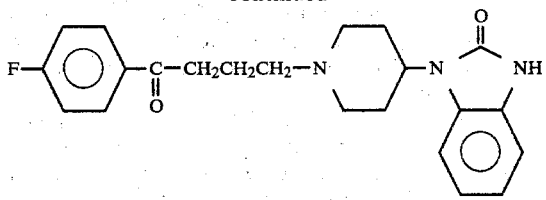

droperidol

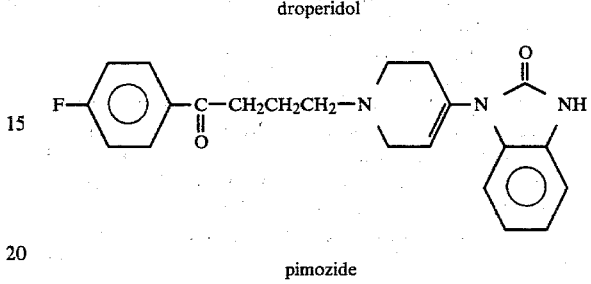

pimozide

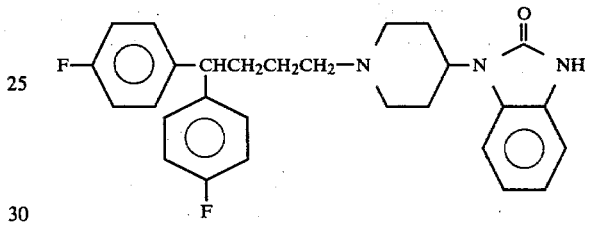

Further, Japanese Published Patent Application No. 160371/1979 and WO 80/00024 published on Jan. 10, 1980 disclose piperidine derivatives having a hypotensive activity. Representative ones of the piperidine derivatives are represented by the following formula:

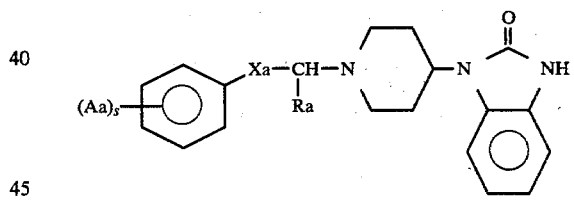

wherein Aa is methoxy or two Aa groups may combine to form methylenedioxy; s is 0 or an integer of 1–3; (Xa is carbonyl, hydroxymethylene or methylene; and Ra is hydrogen or methyl). A U.S. application based on the PCT application is pending (U.S. patent application Ser. No. 191,339 filed on Jan. 31, 1980).

Further, piperidine derivatives having a hypotensive activity are disclosed in U.S. patent application Ser. No. 209,284 filed on Nov. 21, 1980.

Some of the inventors of the above applications are common with the present invention.

Compounds having excellent pharmacological activities are always in demand. In order to obtain such compounds, studies have been made on piperidine derivatives and as a result, it has been found that novel piperidine derivatives represented by the formula [I] have a hypotensive activity. Further, it has been found that some compounds in the compounds represented by the formula [I] have an antiulcer activity, an antiplatelet aggregation activity, a cholesterol-lowering activity, antihistaminic activity or trachea relaxant activity.

The present invention relates to the compounds represented by the above formula [I] (hereinafter referred to as Compound [I] and terms like this shall apply to other compounds), acid addition salts thereof and their use as medicine.

Halogen in the definition of A and $R_3$ in Compound [I] includes chlorine, bromine, etc. The term "lower" in the definition of the various groups in Compound [I] means having 1–5 carbon atoms, especially 1–3, except for "lower alkoxycarbonyl" which has 2–6 carbon atoms, especially 2–4.

Compound [I] includes all of the optical isomers.

Examples of pharmacologically acceptable acid addition salts of Compound [I] are inorganic acid addition salts such as hydrochloride, hydrobromide, hydroiodide, nitrate, sulfate and phosphate, and organic acid addition salts such as acetate, benzoate, maleate, fumarate, succinate, tartrate, citrate, oxalate, glyoxylate, aspartate, methanesulfonate, ethanesulfonate, propanesulfonate, methanedisulfonate, $\alpha,\beta$-ethanedisulfonate and benzenesulfonate.

Especially preferable compounds with the formula representing Compound [I] are represented by the formula [I']:

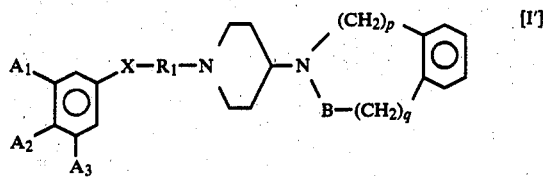

wherein $A_1$, $A_2$ and $A_3$ each are the same group or each are a different group, and $A_1$, $A_2$ and $A_3$ are hydrogen or have the same definition as that of the above-mentioned A group in Formula [I]; and X, $R_1$, p, q and B have the same meaning or definition as described in Formula [I].

Examples of Compound [I] are tabulated in the following Table 1. Table 2 shows structures and Tables 3-1, 2 and 3 show properties of the present compounds.

TABLE 1

| Compound No. | Compound |
|---|---|
| 1 | 1-(3,4-dimethyoxybenzoylmethyl)-4-(2-oxo-3,4-dihydro-2H-1,3-benzoxazin-3-yl)piperidine |
| 2 | 1-(3,4-methylenedioxybenzoylmethyl)-4-(2-oxo-3,4-dihydro-2H-1,3-benzoxazin-3-yl)piperidine |
| 3 | 1-[2-(3,4-dimethoxyphenyl)-2-hydroxyethyl]-4-(2-oxo-3,4-dihydro-2H-1,3-benzoxazin-3-yl)piperidine |
| 4 | 1-[2-(3,4-methylenedioxyphenyl)-2-hydroxyethyl]-4-(2-oxo-3,4-dihydro-2H-1,3-benzoxazin-3-yl)piperidine |
| 5 | 1-[1-(3,4-dimethoxybenzoyl)-ethyl]-4-(2-oxo-3,4-dihydro-2H-1,3-benzoxazin-3-yl)piperidine |
| 6 | 1-[3-(3,4-dimethoxyphenyl)-3-hydroxypropan-2-yl]-4-(2-oxo-3,4-dihydro-2H-1,3-benzoxazin-3-yl)piperidine |
| 7 | 1-(3,4,5-trimethoxybenzoylmethyl)-4-(2-oxo-3,4-dihydro-2H-1,3-benzoxazin-3-yl)piperidine |
| 8 | 1-[2-(3,4,5-trimethoxyphenyl)-2-hydroxyethyl]-4-(2-oxo-3,4-dihydro-2H-1,3-benzoxazin-3-yl)piperidine |
| 9 | 1-(3,4-dimethoxybenzoylmethyl)-4-(3,4-dihydro-2,2-dioxo-1H-2,1,3-benzothiadiazin-3-yl)piperidine |
| 10 | 1-[2-(3,4-dimethoxyphenyl)-2-hydroxyethyl]-4-(3,4-dihydro-2,2-dioxo-1H-2,1,3-benzothiadiazin-3-yl)piperidine |
| 11 | 1-(3,4-methylenedioxybenzoylmethyl)-4-(3,4-dihydro-2,2-dioxo-1H-2,1,3-benzothiadiazin-3-yl)piperidine |
| 12 | 1-[2-(3,4-methylenedioxyphenyl)-2-hydroxyethyl]-4-(3,4-dihydro-2,2-dioxo-1H-2,1,3-benzothiadiazin-3-yl)piperidine |
| 13 | 1-(3,4-dimethoxybenzoylmethyl)-4-(3,4-dihydro-2,2-dioxo-1H-2,1,3-benzothiadiazin-1-yl)piperidine |
| 14 | 1-(3,4-methylenedioxybenzoylmethyl)-4-(3,4-dihydro-2,2-dioxo-1H-2,1,3-benzothiadiazin-1-yl)piperidine |
| 15 | 1-[2-(3,4-dimethoxyphenyl)-2-hydroxyethyl]-4-(3,4-dihydro-2,2-dioxo-1H-2,1,3-benzothiadiazin-1-yl)piperidine |
| 16 | 1-[2-(3,4-methylenedioxyphenyl)-2-hydroxyethyl]-4-(3,4-dihydro-2,2-dioxo-1H-2,1,3-benzothiadiazin-1-yl)piperidine |
| 17 | 1-[1-(3,4-dimethoxybenzoyl)ethyl]-4-(3,4-dihydro-2,2-dioxo-1H-2,1,3-benzothiadiazin-1-yl)piperidine |
| 18 | 1-[3-(3,4-dimethoxyphenyl)-3-hydroxypropan-2-yl]-4-(3,4-dihydro-2,2-dioxo-1H-2,1,3-benzothiadiazin-1-yl)piperidine |

TABLE 2

Structure of compound

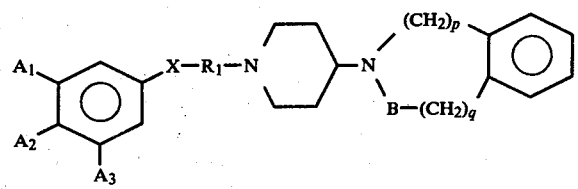

| Compound No. | $A_1$ | $A_2$ | $A_3$ | X | $R_1$ | B | p | q |
|---|---|---|---|---|---|---|---|---|
| 1 | OMe | OMe | H | —C(=O)— | —CH$_2$— | —C(=O)—O— | 1 | 0 |
| 2 | O–CH$_2$–O | | H | —C(=O)— | —CH$_2$— | —C(=O)—O— | 1 | 0 |

TABLE 2-continued

Structure of compound

A₁, A₂, A₃ substituted phenyl—X—R₁—N(piperidine)—N(—(CH₂)ₚ—phenyl—(CH₂)_q—B—)

| Compound No. | A₁ | A₂ | A₃ | X | R₁ | B | p | q |
|---|---|---|---|---|---|---|---|---|
| 3 | OMe | OMe | H | —CH(OH)— | —CH₂— | —C(=O)—O— | 1 | 0 |
| 4 | O—CH₂—O | | H | —CH(OH)— | —CH₂— | —C(=O)—O— | 1 | 0 |
| 5 | OMe | OMe | H | —C(=O)— | —CH(Me)— | —C(=O)—O— | 1 | 0 |
| 6 | OMe | OMe | H | —CH(OH)— | —CH(Me)— | —C(=O)—O— | 1 | 0 |
| 7 | OMe | OMe | OMe | —C(=O)— | —CH₂— | —C(=O)—O— | 1 | 0 |
| 8 | OMe | OMe | OMe | —CH(OH)— | —CH₂— | —C(=O)—O— | 1 | 0 |
| 9 | OMe | OMe | H | —C(=O)— | —CH₂— | —SO₂—NH— | 1 | 0 |
| 10 | OMe | OMe | H | —CH(OH)— | —CH₂— | —SO₂—NH— | 1 | 0 |
| 11 | O—CH₂—O | | H | —C(=O)— | —CH₂— | —SO₂—NH— | 1 | 0 |
| 12 | O—CH₂—O | | H | —CH(OH)— | —CH₂— | —SO₂—NH— | 1 | 0 |
| 13 | OMe | OMe | H | —C(=O)— | —CH₂— | —SO₂—NH— | 0 | 1 |
| 14 | O—CH₂—O | | H | —C(=O)— | —CH₂— | —SO₂—NH— | 0 | 1 |
| 15 | OMe | OMe | H | —CH(OH)— | —CH₂— | —SO₂—NH— | 0 | 1 |
| 16 | O—CH₂—O | | H | —CH(OH)— | —CH₂— | —SO₂—NH— | 0 | 1 |
| 17 | OMe | OMe | H | —C(=O)— | —CH(Me)— | —SO₂—NH— | 0 | 1 |

TABLE 2-continued

Structure of compound

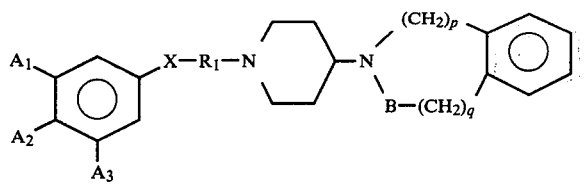

| Compound No. | A₁ | A₂ | A₃ | X | R₁ | B | p | q |
|---|---|---|---|---|---|---|---|---|
| 18 | OMe | OMe | H | —CH(OH)— | —CH(Me)— | —S(O₂)—NH— | 0 | 1 |

TABLE 3

Properties (Melting point: IR, NMR and Elementary analysis)

(1) The term "form" means the state of a compound subjected to the determination of properties.
Blank: free base
EtOH: ethanol of crystallization
HCl: hydrochloride
(2) The values in the column of infrared absorption spectrum (IR) show characteristic maximum absorption of the compounds measured in KBr tablet.
(3) The values in the table of nuclear magnetic resonance spectrum (NMR) and δ values based on TMS in CDCl₃
(Compound Nos. 1–10, 13 and 15), d₆-dimethylsulfoxide (d₆-DMSO)
(Compound Nos. 11, 12, 14 and 16) or CD₃OD+D₂O
(Compound Nos. 17 and 18)
(4) Elementary analysis
A: Calculated
F: Found

TABLE 3-1

| Compound No. | Form | m.p. (°C.) | IR (cm⁻¹) |
|---|---|---|---|
| 1 | | 143.0–144.5 | 1680, 1715 1735 |
| 2 | | 163.0–164.0 | 1680, 1710 1720(sh) |
| 3 | | 169.0–170.0 | 1715 |
| 4 | | 185.7–186.2 | 1715 |
| 5 | | 149.0–151.5 | 1715, 1720(sh) 1680 |
| 6 | | 201.0–202.0 | 1700 |
| 7 | | 152.0–153.5 | 1690, 1720 |
| 8 | | 203.0–204.0 | 1705 |
| 9 | | 173.5–175.5 | 1670, 1345, 1170 |
| 10 | | 171.0–172.5 | 1350, 1340, 1170 |
| 11 | | 184.0–185.5 | 1680, 1342, 1170 |
| 12 | | 178.0–179.0 | 1350, 1340, 1170 |
| 13 | 3/2 EtOH | 102.0–104.0 | 1680, 1350, 1340, 1170 |
| 14 | | 185.0–187.0 | 1685, 1335, 1165 |
| 15 | | 144.5–146.0 | 1350, 1340, 1180 |
| 16 | | 194.5–195.0 | 1345, 1175 |
| 17 | HCl.EtOH | 229.0–231.5 | 1660, 1348, |

TABLE 3-1-continued

| Compound No. | Form | m.p. (°C.) | IR (cm⁻¹) |
|---|---|---|---|
| | | | 1332, 1160 |
| 18 | HCl | 221.0–222.0 | 1350(sh), 1342, 1165 |

TABLE 3-2

| Compound No. | Form | NMR (ppm) |
|---|---|---|
| 1 | | 1.5–2.6, 2.9–3.4, 3.80, 3.93, 4.40, 6.8–7.8 |
| 2 | | 1.6–2.6, 2.9–3.4, 3.73, 4.37, 6.03, 6.73–7.70 |
| 3 | | 1.6–3.50, 2.50(d), 3.83, 3.86, 4.36, 4.13–4.83, 6.70–7.46 |
| 4 | | 1.6–4.1, 4.1–4.83, 4.40, 5.93, 6.60–7.50 |
| 5 | | 1.30(d), 1.50–3.30, 3.96, 4.35, 3.70–4.60, 6.80–7.90 |
| 6 | | 0.78(d), 1.60–3.30, 3.86, 3.90, 4.41, 3.60–4.60, 6.66–7.46 |
| 7 | | 1.30–2.63, 2.83–3.36, 3.86, 3.93, 4.40, 4.1–4.6, 6.9–7.5 |
| 8 | | 1.50–3.60, 2.53(d), 3.83, 3.86, 4.40, 4.06–4.86, 6.60, 6.80–7.46 |
| 9 | | 1.50–2.50, 2.80–3.30, 3.75, 3.90, 3.93, 4.67, 6.20–7.75 |
| 10 | | 1.43–2.0, 2.10–3.33, 3.50–4.10, 3.86, 4.36–5.20, 4.70, 6.50–7.36 |
| 11 | | 1.30–3.10, 3.20–3.90, 3.67, 4.66, 6.10, 6.6–7.7 |
| 12 | | 1.30–2.43, 2.66–3.13, 3.20–3.76, 4.36–4.80, 5.93, 6.56–7.30 |
| 13 | 3/2 EtOH | 1.53–2.60, 2.76–3.40, 3.75, 3.90, 3.93, 4.46, 5.13(broad), 6.73–7.73 |
| 14 | | 1.53–2.40, 2.70–3.40, 3.53–4.13, 3.73, 4.36, 6.12, 6.90–7.76 |
| 15 | | 1.70–3.33, 3.81, 3.85, 3.90–4.76, 4.41, 6.63–7.50 |
| 16 | | 1.46–2.60, 2.76–3.46, 3.60–4.13, 4.20–5.10, 4.40, 5.96, 6.60–7.80 |
| 17 | HCl.EtOH | 1.50(d), 2.10–2.80, 3.06–3.70, 3.96, 4.0, 4.56, 5.28(quartet), 7.10–7.93 |
| 18 | HCl | 1.25(d), 2.12–2.75, 3.05–4.18, 3.89, 4.56, 5.43(broad), 6.92–7.47 |

TABLE 3-3

| | | A: Calculated, F: Found | | | |
|---|---|---|---|---|---|
| Compound No. | Rational formula | | Elementary analysis (%) | | |
| | | | C | H | N |
| 1 | C₂₃H₂₆N₂O₅ | A | 67.30 | 6.39 | 6.82 |
| | | F | 67.11 | 6.51 | 6.64 |
| 2 | C₂₂H₂₂N₂O₅ | A | 66.99 | 5.62 | 7.10 |
| | | F | 67.05 | 5.59 | 6.96 |

TABLE 3-3-continued

A: Calculated, F: Found

| Compound No. | Rational formula | | Elementary analysis (%) | | |
|---|---|---|---|---|---|
| | | | C | H | N |
| 3 | $C_{23}H_{28}N_2O_5$ | A | 66.97 | 6.84 | 6.79 |
| | | F | 66.97 | 6.87 | 6.77 |
| 4 | $C_{22}H_{24}N_2O_5$ | A | 66.65 | 6.10 | 7.07 |
| | | F | 66.61 | 6.01 | 7.04 |
| 5 | $C_{24}H_{28}N_2O_5$ | A | 67.91 | 6.65 | 6.60 |
| | | F | 67.73 | 6.76 | 6.40 |
| 6 | $C_{24}H_{30}N_2O_5$ | A | 67.59 | 7.09 | 6.57 |
| | | F | 67.67 | 7.27 | 6.52 |
| 7 | $C_{24}H_{28}N_2O_6$ | A | 65.44 | 6.41 | 6.36 |
| | | F | 65.62 | 6.51 | 6.23 |
| 8 | $C_{24}H_{30}N_2O_6$ | A | 65.14 | 6.83 | 6.33 |
| | | F | 65.30 | 7.00 | 6.26 |
| 9 | $C_{22}H_{27}N_3O_5S$ | A | 59.31 | 6.11 | 9.43 |
| | | F | 59.45 | 6.14 | 9.17 |
| 10 | $C_{22}H_{29}N_3O_5S$ | A | 59.04 | 5.53 | 9.39 |
| | | F | 59.31 | 6.63 | 9.09 |
| 11 | $C_{21}H_{23}N_3O_5S$ | A | 58.59 | 5.62 | 9.76 |
| | | F | 58.87 | 5.38 | 9.49 |
| 12 | $C_{21}H_{25}N_3O_5S$ | A | 58.32 | 6.06 | 9.72 |
| | | F | 58.58 | 5.94 | 9.57 |
| 13 | $C_{22}H_{27}N_3O_5S \cdot 3/2EtOH$ | A | 58.35 | 7.05 | 8.16 |
| | | F | 58.61 | 6.83 | 8.12 |
| 14 | $C_{21}H_{23}N_3O_5S$ | A | 58.59 | 5.62 | 9.76 |
| | | F | 58.81 | 5.39 | 9.58 |
| 15 | $C_{22}H_{29}N_3O_5S$ | A | 59.04 | 6.53 | 9.39 |
| | | F | 59.31 | 6.58 | 9.31 |
| 16 | $C_{21}H_{25}N_3O_5S$ | A | 58.32 | 6.06 | 9.72 |
| | | F | 58.08 | 5.86 | 9.33 |
| 17 | $C_{23}H_{29}N_3O_5S \cdot HCl \cdot EtOH$ | A | 55.39 | 6.69 | 7.75 |
| | | F | 55.19 | 6.57 | 8.05 |
| 18 | $C_{23}H_{31}N_3O_5S \cdot HCl$ | A | 55.47 | 6.48 | 8.44 |
| | | F | 55.50 | 6.70 | 8.18 |

Hypotensive activity and acute toxicity of Compound [I] are illustrated below as experiments.

Experiment 1

This experiment is conducted according to the method described in "Spontaneously Hypertensive Rats (SHR) Guidelines for Breeding, Care and Use" (published by SHR Conference) (1976) p. 11.

Five spontaneously hypertensive rats (15 weeks old, 180 mmHg or more in blood pressure) are used as one group. Each of the test compound is added to 0.3% (w/v) CMC aqueous solution in a concentration of 3 mg/ml. Each of the mixtures is orally administered to the rats in a dose of 1 ml/100 g. Changes in blood pressure are measured according to the method of tail artery plethysmography (see the literature cited above). The maximum reduction (mmHg) in blood pressure after the administration on the basis of the pressure immediately before the administration is shown in Table 4.

TABLE 4

| Compound No. | Maximum reduction in blood pressure (mmHg) | Compound No. | Maximum reduction in blood pressure (mmHg) |
|---|---|---|---|
| 1 | 40*2 | 10 | 15 |
| 2 | 3 | 11 | 17 |
| 3 | 25*1 | 12 | 27 |
| 4 | 30*1  45*2 | 13 | 22 |
| 5 | 3 | 14 | 30 |
| 6 | 17 | 15 | 30 |
| 7 | 13 | 16 | 18 |
| 8 | 12 | 17 | 17 |
| 9 | 25 | 18 | 10 |

*1 25 mg/kg administration
*2 50 mg/kg administration

Experiment 2

The compound of Compound No. 16 is used as a test compound. Three male dd-strain mice (weight 20±1 g) are used for the test compound.

The compound is added to aqueous physiological sodium chloride, and the mixture is orally (P.O.) administered to the mice in a dose of 1000 mg/kg. After the observation for 7 days, the number of deaths is counted. The result is that no death is observed.

Now, the process for preparing Compound [I] is described below.

Compound [I] may be prepared by reacting a compound represented by the formula [II]:

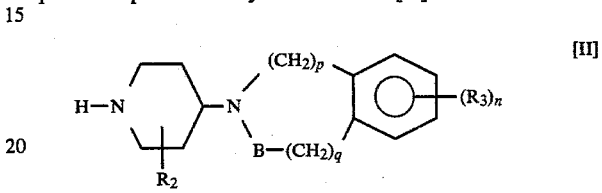

(wherein, $R_2$, p, q, B, $R_3$ and n have the same definitions as defined above) or Compound [II] wherein $R_3$ is protected, with a compound represented by the formula [III]

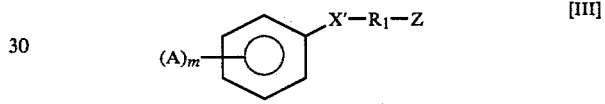

(wherein A, m and $R_1$ have the same definitions as defined above; X' is oxygen, sulfur, carbonyl or methylene; and Z is halogen or an eliminable group) or Compound [III] wherein A is protected, and further if necessary, by reducing the resulting product and if necessary, by eliminating the protective group therefrom.

In the definition of Z, halogen includes chlorine, bromine or iodine; and the eliminable group includes alkylsulfonyloxy (for example, methanesulfonyloxy), arylsulfonyloxy (for example, benzenesulfonyloxy or p-toluenesulfonyloxy), etc.

The reaction of Compound [II] or the protected one with Compound [III] or the protected one is carried out in an inert solvent. Ketone (e.g. acetone), halogenated hydrocarbon (e.g. chloroform and methylene chloride), amide (e.g. dimethylformamide), sulfoxide (e.g. dimethylsulfoxide), substituted or unsubstituted aromatic hydrocarbon (e.g. benzene, toluene and chlorobenzene), lower alcohol (e.g. methanol, ethanol and isopropanol), etc. may be used alone or in combination as an inert solvent. The reaction is carried out at 0°–150° C., preferably at a temperature between room temperature and the boiling point of the solvent depending on the reactivity of the group Z which is exchangeable. The reaction usually proceeds very smoothly in the presence of a base such as lower alcoholate (e.g. sodium methylate and sodium ethylate), alkali hydroxide (e.g. sodium hydroxide), alkali carbonate (e.g. sodium carbonate and potassium carbonate), tertiary amine (e.g. triethylamine and pyridine), etc. The amount of the base is usually 1.0 to 1.2 times the equivalent amount based on Compound [II]. When an acid addition salt of Compound [II] such as hydrochloride is used, it goes without saying that the base supplementary enough to neutralize the acid is added thereto. Use of reaction-promoting agents such as potassium iodide is effective for smooth proceeding of the reaction.

When either $R_3$ or A, or both is(are) hydroxy, amino or lower alkylamino, these groups are protected in a conventional manner prior to the above reaction. After completion of the reaction, the protective group is eliminated in a conventional manner to obtain the desired product.

When X' is carbonyl, the resulting product is reduced to obtain Compound [I] wherein X is hydroxymethylene. The reaction may be carried out by reacting Compound [I] wherein X is carbonyl with a complex metal hydride such as sodium borohydride in a lower alcohol such as methanol, ethanol and isopropanol at $-10°$ to $100°$ C., preferably at a temperature between $0°$ C. and the boiling point of the used solvent. Alternatively, the reaction may be carried out by subjecting Compound [I] wherein X is carbonyl to catalytic reduction using hydrogenating catalyst such as palladium carbon, Raney nickel, platinum black, platinum carbon and platinum oxide in lower alcohol such as methanol and ethanol, lower aliphatic acid such as acetic acid, water or a mixed solvent thereof. These reactions may be carried out either in an open vessel or in a closed vessel under pressure. When the carbon atom of $R_1$ adjacent to X is an asymmetrical carbon in the above reduction, Compound [I] is stereo-selectively obtained according to the reduction method. That is, Compound [I] in threo form is obtained when a complex metal hydride is used and Compound [I] in erythro form is obtained according to catalytic reduction in an acidic condition. The acidic condition is brought with inorganic acids such as hydrochloric acid or organic acids such as acetic acid, propionic acid and succinic acid.

Compound [II] used as a starting compound of Compound [I] is also a new compound. Compound [II] is classified as described in Table 5 for convenience.

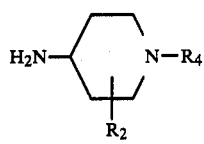

(wherein, $R_2$ has the same definitions as defined above and $R_4$ is a protective group for an amino group) is reacted with a salicylaldehyde or a derivative thereof represented by the formula [V]:

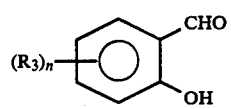

(wherein, $R_3$ and n have the same definitions as defined above) to prepare a compound represented by the formula [VI]:

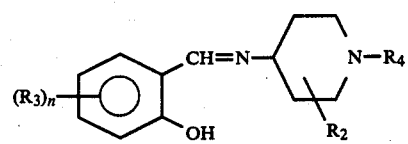

(wherein, $R_2$, $R_3$, $R_4$ and n have the same meaning as defined above).

Examples of the substituents $R_4$ in the Compound [IV] are acyl (e.g. acetyl and benzoyl), alkyloxycarbonyl (e.g. tert.-butoxycarbonyl and ethoxycarbonyl), benzyl, tosyl and mesyl. The reaction can be carried out either without any solvent or in a lower alkanol (e.g. methanol, ethanol and propanol), an aromatic hydrocarbon (e.g. benzene, toluene and xylene), a halogenated hydrocarbon (e.g. methylene chloride and chloroform) or a mixture thereof.

The reaction in an alkanol has the advantage that the conversion to a compound represented by the formula

TABLE 5

| p | q | B | Compound No. | Formula |
|---|---|---|---|---|
| 1 | 0 | $-\underset{\underset{O}{\|\|}}{C}-O-$ | II-1 | ![structure] H—N piperidine(R2)—N—CH2—C6H4(R3)n with O=C—O linkage |
| 1 | 0 | $-\underset{O_2}{S}-NH-$ | II-2 | H—N piperidine(R2)—N—CH2—C6H4(R3)n with S(O2)—N linkage |
| 0 | 1 | $-\underset{O_2}{S}-NH-$ | II-3 | H—N piperidine(R2)—N—CH2— with $O_2$S—NH linkage to C6H4(R3)n |

Compound [II-1] is produced as shown below. First, an 4-amino-piperidine derivative represented by the formula [IV]:

[VII] below can be carried out without isolation of Compound [VI] from the reaction solution. As regards the amounts of the reactants to be used, it is proper to use Compound [V] in an amount of 1.0 to 1.2 equivalent weights, preferably 1.0 equivalent weight, of Compound [IV]. Although the reaction proceeds at room temperature in a short time, it may be carried out at an elevated temperature, if necessary.

Then, Compound [VI] is reduced with a complex metal hydride (e.g. sodium borohydride and sodium cyanoborohydride) in a lower alkanol (e.g. methanol, ethanol and isopropanol) to prepare a compound represented by the formula [VII]:

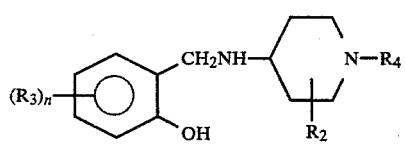

[VII]

(wherein, $R_2$, $R_3$, $R_4$ and n have the same meaning as defined above).

This reaction is advantageously carried out at $-10°$ to $100°$ C., preferably $0°$ C. to room temperature.

Subsequently, Compound [VII] is reacted with a carbonic acid derivative such as phosgene, trichloromethyl chloroformate, alkyl chlorocarbonate, 1,1'-carbonyldiimidazole and urea to prepare a compound represented by the formula [VIII]:

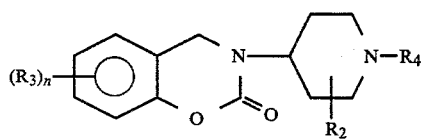

[VIII]

(wherein, $R_2$, $R_3$, $R_4$ and n have the same meaning as defined above).

All of the above reactions can be carried out according to conventional methods and the reaction wherein 1,1'-carbonyldiimidazole is used is particularly described hereinafter. The reaction is carried out in an aprotic polar solvent such as halogenated hydrocarbon (e.g. methylene chloride and chloroform), ether (e.g. ethyl ether, tetrahydrofuran and dioxane), acetonitrile, dimethylformamide and dimethylsulfoxide, in combination thereof or alone, preferably with stirring. Preferably, the amount of 1,1'-carbonyldiimidazole is 1.0 to 2.0 times the equivalent amount based on Compound [VII]. The reaction is carried out at a temperature of from room temperature to the boiling point of the used solvent. The reaction is usually completed in 1 to 3 hours when treated at the boiling point of the solvent and is completed in 10 to 15 hours, when treated at room temperature.

Finally, Compound [VIII] is converted to Compound [II-1] by being subjected to the usual reaction for eliminating the amino-protecting group. The reaction when the amino-protecting group is benzyl is particularly described below. The benzyl-eliminating reaction is carried out by subjecting Compound [VIII] to catalytic reduction in the presence of palladium (e.g. palladium carbon) in a lower alcohol (e.g. methanol, ethanol and isopropanol), water or a mixed solvent thereof. The reaction is preferably carried out in the presence of a mineral acid (e.g. hydrochloric acid, hydrobromic acid, hydroiodic acid and perchloric acid). The proper amount of the mineral acid is 1 to 2 times the equivalent amount based on Compound [VIII]. Proper reaction temperature is room temperature to $50°$ C.

Compound [II-2] is produced as shown below. First, a compound represented by the formula [IX]:

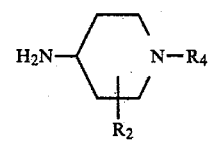

[IX]

(wherein, $R_2$ and $R_4$ have the same meaning as defined above) is reacted with a compound represented by the formula [X]:

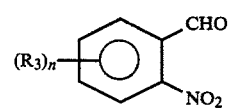

[X]

(wherein, $R_3$ and n have the same meaning as defined above) to prepare a compound represented by the formula [XI]:

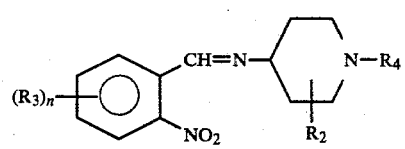

[XI]

(wherein, $R_2$, $R_3$, $R_4$ and n have the same meaning as defined above).

This reaction can be carried out in the same manner as that in the preparation of Compound [VI] from Compounds [IV] and [V].

Then, Compound [XI] is reduced to prepare a compound represented by the formula [XII]:

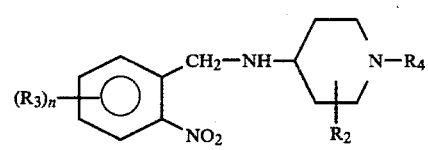

[XII]

(wherein, $R_2$, $R_3$, $R_4$ and n have the same significance as defined above).

This reaction can be carried out in the same manner as that in the preparation of Compound [VII] from Compound [VI].

Then, Compound [XII] is further reduced to prepare a compound represented by the formula [XIII]:

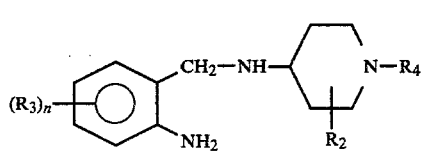

[XIII]

(wherein, $R_2$, $R_3$, $R_4$ and n have the same meaning as defined above).

This reaction can be performed by the methods generally adopted for the purpose of reducing a nitro group into an amino group, for example, the method involving combined use of a metal such as Sn, Fe or Zn and a mineral acid such as hydrochloric acid and sulfuric acid or an organic acid such as acetic acid, the method resorting to use of a sulfide or hydrazine and the catalytic reduction in the presence of a catalyst such as palladium carbon. When the reduction is performed by the catalytic method, the reaction is effected by causing the Compound [XII] to absorb an equivalent weight of hydrogen in water, a lower alkanol such as methanol and ethanol, or a mixture thereof. The reaction is preferably carried out from 20° C. to 60° C., especially around room temperature.

Compound [XIII] is reacted with sulfurylamide (H₂NSO₂NH₂) to prepare a compound represented by the formula [XIV]:

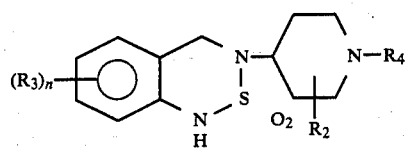

[XIV]

(wherein, $R_2$, $R_3$, $R_4$ and n have the same meaning as defined above).

This reaction is performed in pyridine. As concerns the amounts of the reactants involved in this reaction, it is advantageous to use the sulfurylamide in the amount of 1.0 to 4.0 equivalent weights of Compound [XIII]. The reaction is generally performed under thermal reflux and is completed in a period of 2 to 10 hours.

Finally, Compound [XIV] is converted into Compound [II-2] by eliminating the group $R_4$ by the usual methods, for example in the same manner as that in the conversion of Compound [VIII] to Compound [II-1].

Compound [II-3] is produced as shown below. First, a 4-oxo-piperidine derivative represented by the formula [XV]:

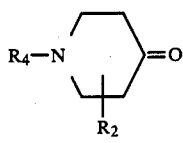

[XV]

(wherein, $R_2$ and $R_4$ have the same definitions as defined above) is reacted with a compound represented by the formula [XVI]:

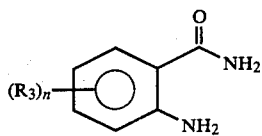

[XVI]

(wherein, $R_3$ and n have the same definitions as defined above) in an aromatic hydrocarbon type solvent such as benzene, toluene and xylene in the presence of sulfuric acid, an alkane-sulfonic acid (e.g. methanesulfonic acid) or an aryl-sulfonic acid (e.g. p-toluenesulfonic acid) as a catalyst to prepare a compound represented by formula [XVII]:

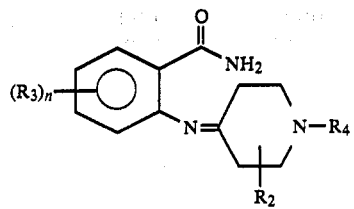

[XVII]

(wherein, $R_2$, $R_3$, $R_4$ and n have the same definitions as defined above).

The reaction is advantageously performed by using p-toluenesulfonic acid as a catalyst and removing the water through distillation under reflux.

Compound [XVII] is then reduced with a complex metal hydride, preferably lithium aluminum hydride, in an ether solvent such as ethyl ether, dioxane and tetrahydrofuran to prepare a compound represented by the formula [XVIII]:

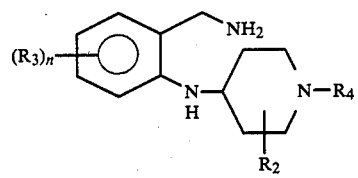

[XVIII]

(wherein, $R_2$, $R_3$, $R_4$ and n have the same definitions as defined above).

It is advantageous to use the complex methanol hydride in the amount of 1.0 to 10, especially 2 to 6 equivalent weights of Compound [XVII]. The reaction is preferably carried out from room temperature to 150° C., especially from 50° to 120° C. The reaction is usually completed in 2 to 24 hours though it can be completed in shorter time according to the used compounds.

Compound [XVIII] is reacted with sulfurylamide to prepare a compound represented by the formula [XIX]:

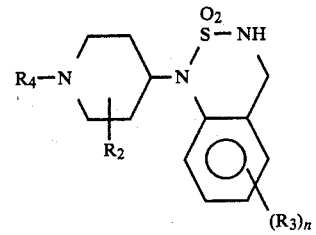

[XIX]

(wherein, $R_2$, $R_3$, $R_4$ and n have the same definitions as defined above).

This reaction can be carried out in the same manner as that in the preparation of Compound [XIV] from Compound [XIII].

Finally, Compound [XIX] is converted into Compound [II-3] by eliminating the group $R_4$ by the usual methods, for example in the same manner as that in the conversion of Compound [VIII] to Compound [II-1].

Isolation and purification of Compound [I] as well as the above-mentioned intermediates are carried out according to conventional methods in the field of organic synthetic chemistry, for example, concentration, extraction, recrystallization and chromatography. Specifically, since Compound [I] readily crystallizes in general, it can be isolated and purified by distilling off the solvent from the reaction mixture and recrystallizing the residue from a suitable solvent such as ethanol.

A pharmacologically acceptable acid addition salt of Compound [I] may be obtained by reacting Compound [I] with a suitable acid in a suitable solvent such as ethanol.

The pharmaceutical compositions of the present invention are described below.

It is obvious from the foregoing various experimental data that Compound [I] has a hypotensive activity.

In view of the hypotensive activity, the compounds of the present invention may be used in various pharmaceutical forms for administration. Pharmaceutical compositions of the present invention are prepared by uniformly mixing an effective amount of the compound in the form of a base or an acid addition salt as an active ingredient with a pharmaceutically acceptable carrier. According to the pharmaceutical forms suitable for administration, the carrier may take various forms. It is desirable that the pharmaceutical compositions are in single administration form suitable for administration per os or by injection.

In preparation of the composition for oral administration, any useful pharmaceutical carrier may be used. For example, water, glycols, oils, alcohols, etc. may be used to prepare oral liquid preparations such as suspensions and syrups, and excipients, lubricants, binders, disintegrators, etc. may be used to prepare powders, pills, capsules and tablets. Examples of the carriers are glucose and lactose as the excipients, starch and sodium alginate as the disintegrators, magnesium stearate, paraffin sulfate and talc as the lubricants, and syrup, ethanol and gelatin as the binders. The active ingredient is orally administered in a dose of 1–100 mg, particularly 10–60 mg, per day for an adult.

The preparation of Compound [I] and the present pharmaceutical compositions are illustrated by the following examples, and the preparation of the intermediates is illustrated by the following reference examples.

EXAMPLE 1

1-(3,4-Dimethoxybenzoylmethyl)-4-(2-oxo-3,4-dihydro-2H-1,3-benzoxazin-3-yl)-piperidine In this example, 4.03 g of 4-(2-oxo-3,4-dihydro-2H-1,3-benzoxazin-3-yl)-piperidine hydrochloride, 3.88 g of ω-bromo-3,4-dimethoxy-acetophenon, 4.2 ml of triethylamine and 30 ml of N,N-dimethylformamide are mixed and stirred at room temperature for 2 hours and 30 minutes. Subsequently, the reaction mixture is poured into 150 ml of ice water and stirred therein for 3 hours. The crystals deposited are separated by filtration and dried to obtain 5.36 g of a crude product. The crude product is recrystallized from hot ethanol to obtain 4.94 g of the desired product. Physical properties of the product are shown in Tables 3-1, 3-2 and 3-3, and so are physical properties of the compounds obtained in the following examples.

EXAMPLE 2

1-(3,4-Methylenedioxybenzoylmethyl)-4-(2-oxo-3,4-dihydro-2H-1,3-benzoxazin-3-yl)-piperidine In this example, 4.03 g of 4-(2-oxo-3,4-dihydro-2H-1,3-benzoxazin-3-yl)-piperidine hydrochloride, 3.64 g of ω-bromo-3,4-methylenedioxy-acetophenone, 4.2 ml of triethylamine and 30 ml of N,N-dimethylformamide are mixed and stirred at room temperature for 2 hours and 30 minutes. Subsequently, the reaction mixture is poured into 150 ml of ice water and stirred therein for 3 hours. The crystals deposited are separated by filtration and dried to obtain 5.43 g of a crude product. The crude product is recrystallized from hot ethanol to obtain 4.82 g of the desired product.

EXAMPLE 3

1-[2-(3,4-Dimethoxyphenyl)-2-hydroxyethyl]-4-(2-oxo-3,4-dihydro-2H-1,3-benzoxazin-3-yl)-piperidine In this example, 3.0 g of 1-(3,4-dimethoxybenzoylmethyl)-4-(2-oxo-3,4-dihydro-2H-1,3-benzoxazin-3-yl)-piperidine obtained in Example 1 is mixed with 150 ml of methanol. While this mixture is stirred at 0°–10° C., 0.8 g of sodium borohydride is added thereto over a period of 3 hours. The reaction solution is stirred overnight at room temperature. Then, the solution is further mixed with 0.4 g of sodium borohydride and stirred at room temperature for 3 hours. The white crystals deposited are separated by filtration, washed with methanol and water and dried to obtain 2.77 g of a crude product. The crude product is recrystallized from ethanol to obtain 2.52 g of the desired product.

EXAMPLE 4

1-[2-(3,4-Methylenedioxyphenyl)-2-hydroxyethyl]-4-(2-oxo-3,4-dihydro-2H-1,3-benzoxazin-3-yl)-piperidine In this example, 3.0 g of 1-(3,4-methylenedioxybenzoylmethyl)-4-(2-oxo-3,4-dihydro-2H-1,3-benzoxazin-3-yl)-piperidine obtained in Example 2 is mixed with 150 ml of methanol. While the mixture is stirred at 0° to 10° C., 0.8 g of sodium borohydride is added thereto over a period of 3 hours. Then, the mixture is stirred overnight at room temperature. The mixture is further mixed with 0.4 g of sodium borohydride and stirred at room temperature for 3 hours. The white crystals deposited are separated by filtration, washed with methanol and water and dried to obtain 2.36 g of a crude product. In the meantime, the filtrate is concentrated under reduced pressure. The residue is mixed with water. The crystals deposited are separated by filtration, washed with water and dried to obtain 0.37 g of a crude product. The two crude products are combined and recrystallized from ethanol to obtain 2.49 g of the desired product.

EXAMPLE 5

1-[1-(3,4-Dimethoxybenzoyl)-ethyl]-4-(2-oxo-3,4-dihydro-2H-1,3-benzoxazin-3-yl)-piperidine In this example, 4.03 g of 4-(2-oxo-3,4-dihydro-2H-1,3-benzoxazin-3-yl)-piperidine hydrochloride, 4.10 g of α-bromo-3,4-dimethoxypropiophenone, 4.2 ml of triethylamine and 30 ml of N,N-dimethylformamide are mixed and stirred at room temperature for 6 hours. Then, the reaction mixture is poured into 150 ml of ice water. The oily substance formed is separated by decantation of the water phase. The oily substance is dissolved in 100 ml of ethyl acetate. The solution is washed with a saturated aqueous sodium chloride, dried and concentrated under reduced pressure to obtain 5.0 g of a crude product. The crude product is recrystallized from ethanol to obtain 4.21 g of the desired product.

EXAMPLE 6

1-[3-(3,4-Dimethoxyphenyl)-3-hydroxypropan-2-yl]-4-(2-oxo-3,4-dihydro-2H-1,3-benzoxazin-3-yl)-piperidine In this example, 2.8 g of 1-[1-(3,4-dimethoxybenzoyl)-ethyl]-4-(2-oxo-3,4-dihydro-2H-1,3-benzoxazin-3-yl)-piperidine obtained in Example 5 is mixed with 150 ml of methanol. While the mixture is stirred at 0° to 10° C., 2 g of sodium borohydride is added thereto over a period of one hour. The mixture is further stirred for 3 hours at the same temperature and then stirred overnight at room temperature. The white crystals deposited are separated by filtration, washed with methanol and water and dried to obtain 1.90 g of a crude product. The crude product is recrystallized from ethanol to obtain 1.67 g of the desired product.

EXAMPLE 7

1-(3,4,5-Trimethoxybenzoylmethyl)-4-(2-oxo-3,4-dihydro-2H-1,3-benzoxazin-3-yl)-piperidine In this example, 4.03 g of 4-(2-oxo-3,4-dihydro-2H-1,3-benzoxazin-3-yl)-piperidine hydrochloride, 4.33 g of ω-bromo-3,4,5-trimethoxy-acetophenone, 42 ml of triethylamine and 100 ml of methanol are mixed and stirred at room temperature for one hour and 40 minutes. The reaction solution is concentrated under reduced pressure and the residue is mixed with water. The crystals deposited are separated by filtration, washed with water and dried to obtain 5.8 g of a crude product. The crude product is recrystallized from ethanol to obtain 2.75 g of the desired product.

EXAMPLE 8

1-[2-(3,4,5-Trimethoxyphenyl)-2-hydroxyethyl]-4-(2-oxo-3,4-dihydro-2H-1,3-benzoxazin-3-yl)-piperidine In this example, 2.8 g of 1-(3,4,5-trimethoxybenzoylmethyl)-4-(2-oxo-3,4-dihydro-2H-1,3-benzoxazin-3-yl)-piperidine obtained in the same manner as in Example 7 is mixed with 150 ml of methanol. While this mixture is stirred at 0° to 10° C., 1.5 g of sodium borohydride is added thereto over a period of 2 hours. Then, the mixture is stirred overnight at room temperature. The mixture is further mixed with 1 g of sodium borohydride and stirred overnight. The white crystals deposited are separated by filtration, washed with methanol and water and dried to obtain 1.96 g of a crude product. The crude product is recrystallized from ethanol to obtain 1.76 g of the desired product.

EXAMPLE 9

1-(3,4-Dimethoxybenzoylmethyl)-4-(3,4-dihydro-2,2-dioxo-1H-2,1,3-benzothiadiazin-3-yl)-piperidine In this example, 4.56 g of 4-(3,4-dihydro-2,2-dioxo-1H-2,1,3-benzothiadiazin-3-yl)-piperidine hydrochloride, 3.88 g of 3,4-dimethoxy-ω-bromoacetophenone and 3.04 g of triethylamine are dissolved in 100 ml of chloroform. The solution is stirred at room temperature for 2 days. The reaction mixture is washed with water, dried and concentrated under reduced pressure. The residue is mixed with 10 ml of methanol and allowed to stand for one hour. The crystals deposited are separated by filtration, washed with methanol and dried to obtain 2.57 g of crude crystals. The crude crystals are recrystallized from ethanol to obtain 2.35 g of the desired product.

EXAMPLES 10–13

Compounds of Compound Nos. 11, 13, 14 and 17

Since the compounds designated as Compound Nos. 11, 13, 14 and 17 in Table 1 are obtained according to a similar procedure, the procedure for the preparation of compound 13 is exemplified below. Particulars on the other compounds are shown in Table 6.

In 30 ml of N,N-dimethylformamide, 4.545 g (15 m.mols) of 4-(3,4-dihydro-2,2-dioxo-1H-2,1,3-benzothiadiazin-1-yl)-piperidine monohydrochloride, 3.884 g (15 m.mols) of ω-bromo-3,4-dimethoxyacetophenone and 4.2 ml (30 m.mols) of triethylamine are dissolved and the solution is stirred at room temperature for 2 hours and 20 minutes. The reaction solution is mixed with 300 ml of chloroform, washed with water (100 ml×2 and 50 ml×2), washed with a saturated aqueous sodium chloride, dried and concentrated to dryness under reduced pressure. Since the residue still contains N,N-dimethylformamide, it is washed with 80 ml of water added thereto. The water layer is removed by decantation. The residue is mixed with 50 ml of methanol. The solvent is distilled off under reduced pressure. The residual crystals are mixed with 3 ml of methanol and separated by filtration to obtain 5.88 g of crude crystals. The crude crystals are recrystallized from ethanol to obtain 5.55 g of 1-(3,4-dimethoxybenzoylmethyl)-4-(3,4-dihydro-2,2-dioxo-1H-2,1,3-benzothiadiazin-1-yl)-piperidine 3/2C$_2$H$_5$OH (Compound No. 13).

TABLE 6

| Compound No. | Starting compound | Reaction solvent | Base | Solvent for recrystallization | Yield |
|---|---|---|---|---|---|
| 11 | 4-(3,4-Dihydro-2,2-dioxo-1H-2,1,3-benzothiadiazin-3-yl)-piperidine hydrochloride 3.04 g (10 m . mols) | ω-Bromo-3,4-methylene-dioxy-acetophenone 2.43 g (10 m . mols) | DMF 20 ml | Triethylamine 2.8 ml (20 m . mols) | EtOH | 69.5% |
| 13 | 4-(3,4-Dihydro-2,2-dioxo-1H-2,1,3-benzothiadiazin-1-yl)-piperidine hydrochloride 5.454 g (15 m . mols) | ω-Bromo-3,4-dimethoxy-acetophenone 3.884 g (15 m . mols) | DMF 30 ml | Triethylamine 4.2 ml (30 m . mols) | EtOH | 83.2% |
| 14 | Same as above 4.545 g | ω-Bromo-3,4-methylene- | DMF 30 ml | Triethylamine 4.2 ml | EtOH | 68.3% |

TABLE 6-continued

| Compound No. | Starting compound | Reaction solvent | Base | Solvent for recrystallization | Yield |
| --- | --- | --- | --- | --- | --- |
| | (15 m. mols) | dioxy-acetophenone 3.64 g (15 m. mols) | (30 m. mols) | | |
| 17 | Same as above 4.17 g (13.7 m. mols) | α-Bromo-3,4-dimethoxy-propiophenon 3.74 g (13.7 m. mols) | DMF 30 ml | Triethylamine 3.82 ml (27.4 m. mols) | EtOH—$H_2O$ | 31.1% |

(Note) The forms of the compounds are the same as those of Table 3.

EXAMPLES 14–18

Compounds of Compound Nos. 10, 12, 15, 16 and 18

Since the compounds designated as Compound Nos. 10, 12, 15, 16, and 18 in Table 1 are prepared according to a similar procedure, the procedure for the preparation of Compound 10 is exemplified below. Particulars on the other compounds are shown in Table 7.

In 150 ml of methanol, 2.2 g of 1-(3,4-dimethoxybenzoylmethyl)-4-(3,4-dihydro-2,2-dioxo-1H-2,1,3-benzothiadiazin-3-yl)-piperidine is suspended. While this suspension is stirred at room temperature, 1.0 g of sodium borohydride is added thereto by portions over a period of four hours. The mixture is stirred overnight at room temperature and 400 mg of sodium borohydride is added thereto. Then, the mixture is stirred overnight. The reaction solution is concentrated under reduced pressure. The residue is mixed with 100 ml of water and adjusted to pH 9.3 with concentrated hydrochloric acid. The resultant mixture is extracted with chloroform. The organic layer is washed with water, dried and freed from the solvent by distillation to obtain a syrup as a residue. This residue is crystallized by adding methanol thereto. The crystals are separated by filtration to obtain 1.93 g of crude crystals. The crude crystals are recrystallized from ethanol to obtain 1.45 g of 1-[2-(3,4-dimethoxyphenyl)-2-hydroxyethyl]-4-(3,4-dihydro-2,2-dioxo-1H-2,1,3-benzothiadiazin-3-yl)-piperidine (Compound No. 10).

EXAMPLE 19

(Example of preparing 10,000 5 mg-tablets)

Compound 4: 50 g

Magnesium stearate: 4 g

Crystalline cellulose: 746 g

The above-described ingredients are mixed for 5 minutes by means of a mixer. The resulting mixed powder is made into 10,000 tablets of 6.0 mm in diameter, 2.5 mm in thickness, and 80 mg in weight using a tablet-making machine (Model HU-37; made by Kikusui Seisakusho) equipped with a pestle having a plane surface and round corners.

EXAMPLE 20

(Example of preparing a powder)

Compound 14: 110 g

Lactose: 890 g

The above-described ingredients are mixed for 10 minutes using a mixer to obtain a uniform mixture (powder).

REFERENCE EXAMPLE 1

1-Benzyl-4-[N-(o-hydroxybenzyl)-amino]-piperidine

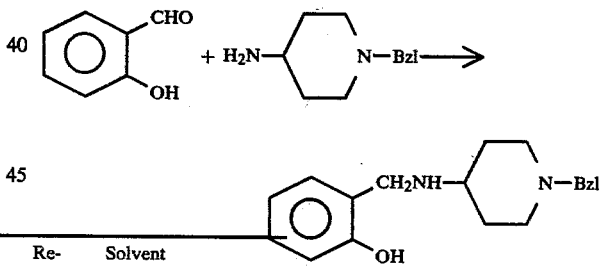

TABLE 7

| Compound No. | Starting compound | Reaction solvent | Reducing agent | Solvent for recrystallization | Yield |
| --- | --- | --- | --- | --- | --- |
| 12 | 1-(3,4-Methylenedioxybenzoylmethyl)-4-(3,4-dihydro-2,2-dioxo-1H-2,1,3-benzothiadiazin-3-yl)-piperidine 2.2 g | MeOH 150 ml | $NaBH_4$ 1.4 g | EtOH | 65.6% |
| 15 | 1-(3,4-Dimethoxybenzoylmethyl)-4-(3,4-dihydro-2,2-dioxo-1H-2,1,3-benzothiadiazin-1-yl)-piperidine 3.0 g | MeOH 150 ml | $NaBH_4$ 1.5 g | EtOH | 82.3% |
| 16 | 1-(3,4-Methylenedioxybenzoylmethyl)-4-(3,4-dihydro-2,2-dioxo-1H-2,1,3-benzothiadiazin-1-yl)-piperidine 3.0 g | MeOH 150 g | $NaBH_4$ 1.5 g | EtOH | 67.3% |
| 18 | 1-[1-(3,4-Dimethoxybenzoyl)-ethyl]-4-(3,4-dihydro-2,2-dioxo-1H-2,1,3-benzothiadiazin-1-yl)-piperidine monohydrochloride 1.7 g | MeOH 100 ml | $NaBH_4$ 2.0 g | EtOH/$H_2O$ | 57.9% |

(Note) The forms of the compounds are the same as those of Table 3.

In this reference example, 9.76 g of salicylaldehyde, 15.12 g of 1-benzyl-4-amino-piperidine and 100 ml of methanol are mixed and stirred at room temperature for one hour. While the resultant mixture is cooled with ice, 3.2 g of sodium borohydride is added thereto over a period of one hour and 30 minutes. Then, the mixture is stirred at room temperature for 2 hours. The resultant reaction mixture is poured into 1 l of ice water. The light yellow crystals deposited are separated by filtration and then dissolved in 200 ml of ethyl acetate. The ethyl acetate solution is washed with a saturated aqueous sodium chloride, dried and subsequently concentrated under reduced pressure to obtain 19.0 g of light yellow crystals. The crystals are recrystallized from ethanol to obtain 12.0 g of the desired product.

Melting point: 92.5°–93.0° C.
Elementary analysis (%): $C_{19}H_{24}N_2O$:

|  | C | H | N |
|---|---|---|---|
| Calculated | 76.99 | 8.16 | 9.45 |
| Found | 76.97 | 8.10 | 9.37 |

REFERENCE EXAMPLE 2

1-Benzyl-4-(2-oxo-3,4-dihydro-2H-1,3-benzoxazin-3-yl)-piperidine

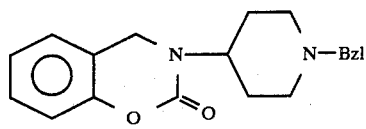

In this reference example, 17.7 g of 1-benzyl-4-[N-(o-hydroxybenzyl)-amino]-piperidine obtained by the procedure of Reference Example 1, 19.4 g of 1,1'-carbonyl-dimidazole and 150 ml of tetrahydrofuran are mixed, stirred for 2 hours and 30 minutes, refluxed and then concentrated under reduced pressure.

Subsequently, the formed crystalline residue is mixed with water and separated by filtration to obtain 18.0 g of crude crystals. The crude crystals are recrystallized from a mixture of n-hexane and ethyl acetate [50:7 (V/V)] to obtain 14.85 g of the desired product.

Melting point: 106.0°–107.0° C.
Elementary analysis (%): $C_{20}H_{22}N_2O_2$:

|  | C | H | N |
|---|---|---|---|
| Calculated | 74.51 | 6.88 | 8.69 |
| Found | 74.80 | 6.98 | 8.74 |

REFERENCE EXAMPLE 3

4-(2-Oxo-3,4-dihydro-2H-1,3-benzoxazin-3-yl)-piperidine hydrochloride

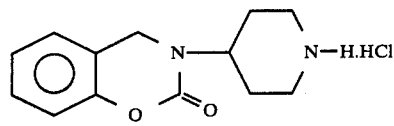

In this reference example, 16.0 g of 1-benzyl-4-(2-oxo-3,4-dihydro-2H-1,3-benzoxazin-3-yl)-piperidine and 4.0 g of 10% palladium carbon are added to a mixture of 150 ml of water, 50 ml of 1 N hydrochloric acid and 300 ml of methanol. While the resultant mixture is stirred, hydrogen gas is passed therethrough overnight. Then, the reaction mixture is filtered and the filtrate is concentrated. The white crystals as a residue are mixed with methanol and separated by filtration to obtain 11.4 g of the desired product.

Melting point: 288.0°–290.0° C.
Elementary analysis (%): $C_{13}H_{17}N_2O_2Cl$:

|  | C | H | N |
|---|---|---|---|
| Calculated | 58.10 | 6.38 | 10.42 |
| Found | 57.92 | 6.40 | 10.26 |

REFERENCE EXAMPLE 4

1-Benzyl-4-[N-(o-nitrobenzyl)-amino]-piperidine dihydrochloride

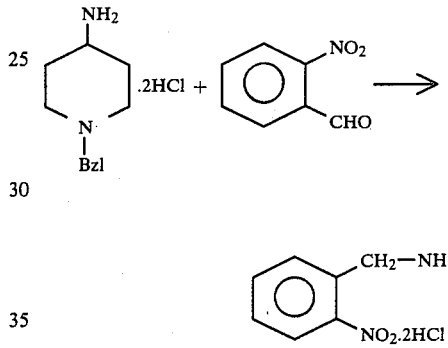

In this reference example, 5.24 g of 1-benzyl-4-amino-piperidine dihydrochloride, 3.02 g of o-nitrobenzaldehyde, 2.02 g of triethylamine and 30 ml of methanol are mixed and stirred at room temperature for one hour. The resultant solution is cooled with ice and stirred. To the stirred solution, 1 g of sodium borohydride is added little by little over a period of one hour. Then, the mixture is brought back to room temperature and stirred at room temperature for 2 hours. The resultant solution is poured into 200 ml of ice water and extracted with ether. The organic layer is washed with water, dried and concentrated. The oily residue is dissolved in 20 ml of ethanol. The solution is mixed with 10 ml of a solution of 5.7 N hydrochloric acid in ethyl acetate. The white crystals deposited are separated by filtration, washed with 20 ml of ethyl acetate and dried to obtain 5.70 g of a crude product. The crude product is recrystallized from hot ethanol to obtain 2.90 g of the desired product.

Melting point: 260.0°–263.5° C.
Elementary analysis (%): $C_{19}H_{25}N_3O_2Cl_2$:

|  | C | H | N |
|---|---|---|---|
| Calculated | 57.29 | 6.33 | 10.55 |
| Found | 57.19 | 6.48 | 10.27 |

REFERENCE EXAMPLE 5

1-Benzyl-4-[N-(o-aminobenzyl)-amino]-piperidine trihydrochloride

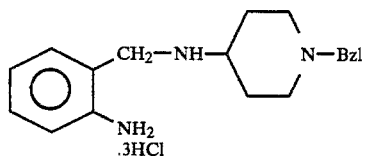

In this reference example, 31.8 g of 1-benzyl-4-[N-(o-nitrobenzyl)-amino]-piperidine dihydrochloride, 3.2 g of 10% Pd-C and 500 ml of water are mixed and stirred at room temperature. Then, about 6 l of hydrogen gas is absorbed by the mixture. Then the reaction is discontinued and the Pd-C is removed by filtration. The aqueous solution is adjusted to pH 11 with an aqueous sodium hydroxide and then extracted with ethyl acetate. The organic layer is washed with water, dried and concentrated. The resulting oily product is dissolved in 140 ml of ethanol. Then, 70 ml of a solution of 5.7 N hydrochloric acid in ethyl acetate is added thereto. The white crystals deposited are separated by filtration, washed with ethyl acetate and dried to obtain 23.5 g of a crude product. The crude product is recrystallized from a mixed solvent of methanol and ethyl acetate to obtain 15.0 g of the desired product.

Melting point: 225.0°–228.0° C.

Elementary analysis (%): $C_{19}H_{28}N_3Cl_3$:

|  | C | H | N |
|---|---|---|---|
| Calculated | 56.37 | 6.97 | 10.38 |
| Found | 56.35 | 7.00 | 10.31 |

REFERENCE EXAMPLE 6

1-Benzyl-4-(3,4-dihydro-2,2-dioxo-1H-2,1,3-benzothiadiazin-3-yl)-piperidine

In this reference example, 1.10 g of 1-benzyl-4-[N-(o-aminobenzyl)-amino]-piperidine trihydrochloride is mixed with 5 ml of water. Then, 15 ml of 1 N aqueous sodium hydroxide is added to the solution with cooling. The mixture is extracted with 20 ml of chloroform four times. The chloroform layer is washed with 20 ml of water two times. The resultant layer is dried and concentrated under reduced pressure to obtain 670 mg of 1-benzyl-4-[N-(o-aminobenzyl)amino]-piperidine as an oily residue.

Then, 590 mg of 1-benzyl-4-[N-(o-aminobenzyl)amino]-piperidine, 600 mg of sulfurylamide and 12 ml of pyridine are mixed and refluxed with heating for 2 hours. The reaction mixture is cooled to room temperature and poured into 50 ml of ice water. The white crystals deposited are separated by filtration, washed with 10 ml of water and dried to obtain 520 mg of the desired product as crystals.

NMR (δ ppm in CDCl$_3$): 1.37–2.27(6H, m), 2.66–3.10 (2H, m), 3.42(2H, s), 3.83(1H, m), 4.62(2H, s), 5.76(1H, s) (exchangeable proton), 6.33–7.46(9H, m).

IR (KBr) $v_{max}^{cm-1}$: 1340, 1165 (SO$_2$) cm$^{-1}$.

REFERENCE EXAMPLE 7

4-(3,4-Dihydro-2,2-dioxo-1H-2,1,3-benzothiadiazin-3-yl)-piperidine

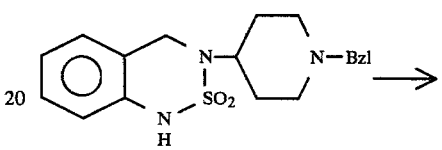

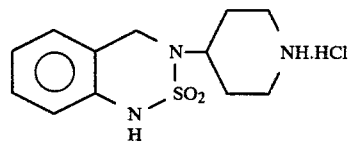

In this reference example, 7.14 g (20 m.mols) of 1-benzyl-4-(3,4-dihydro-2,2-dioxo-1H-2,1,3-benzothiadiazin-3-yl)-piperidine, 2 g of 10% palladium carbon, 20 ml of 1 N hydrochloric acid, 60 ml of water and 120 ml of methanol are mixed. While the mixture is stirred at 40° C., hydrogen gas is blown into the mixture at 40° C. for 20 hours. The reaction mixture is filtered to remove palladium carbon. The filtrate is concentrated to dryness to obtain 5.0 g of the desired product.

NMR (δ ppm in d$_6$DMSO): 1.47–2.20(4H, m), 2.60–4.35 (5H, m), 4.63(2H, s), 6.60–7.40(4H, m), 9.10(2H, broad s) (exchangeable proton), 10.46 (1H, s) (exchangeable proton).

IR (KBr) $v_{max}^{cm-1}$: 1330, 1155 (SO$_2$) cm$^{-1}$.

REFERENCE EXAMPLE 8

1-Benzyl-4-[N-(o-aminomethylphenyl)-amino]piperidine

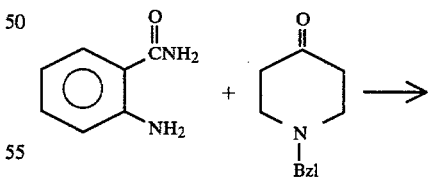

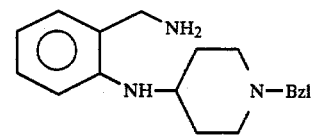

In this reference example, the mixture of 13.6 g of anthranilamide, 18.9 g of 1-benzyl-4-piperidone, 1.0 g of p-toluene-sulfonic acid monohydrate and 200 ml of benzene is refluxed in a Dean Stark apparatus for 6 hours to distil off water. The resultant suspension of the Schiff-base is concentrated. The residue is mixed with 250 ml of dry dioxane to form a suspension. Separately, 100 ml of dry dioxane and 12.4 g of lithium aluminum hydride are mixed. The above Schiff-base suspension is added little by little to the mixture with stirring without cooling. The mixture is stirred for one hour and then refluxed with heating for 18 hours. The reaction solution is cooled to room temperature and poured little by little into 1.3 l of ice water. The resultant suspension is poured little by little into a funnel previously coated with a filter aid and subjected to suction filtration. The cake on the funnel is washed with 500 ml of chloroform and filtered. The organic layer is washed with water, dried and concentrated to obtain 22.9 g of a crude product. The crude product is recrystallized from hot ethanol to obtain 18.7 g of the desired product.

Melting point: 117.0°–118.0° C.

Elementary analysis (%): $C_{19}H_{25}N_3$:

|  | C | H | N |
|---|---|---|---|
| Calculated | 77.25 | 8.53 | 14.22 |
| Found | 77.45 | 8.66 | 13.98 |

REFERENCE EXAMPLE 9

1-Benzyl-4-(3,4-dihydro-2,2-dioxo-2,1,3-benzothiadiazin-1-yl)-piperidine monohydrochloride

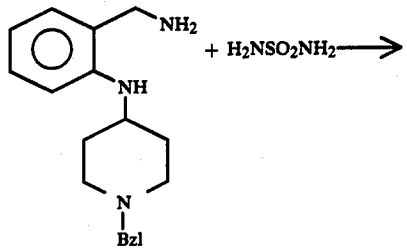

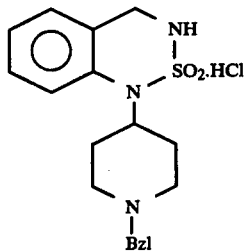

In this reference example, 33.0 g (112.4 m.mols) of 1-benzyl-4-[N-(o-aminomethylphenyl)-amino]-piperidine, 21.6 g (224.8 m.mols) of sulfuryl amide and 250 ml of pyridine are mixed and refluxed with heating for 8 hours. The reaction solution is cooled to room temperature, concentrated to 70 ml and poured into 500 ml of ice water. The mixture is mixed with 300 ml of chloroform, stirred and adjusted to pH 9 with 2 N aqueous sodium hydroxide. The chloroform layer is separated with separating funnel and the remaining water layer is further extracted with chloroform (300 ml×3). The chloroform layers are combined, washed with water (300 ml×4), dried and concentrated to obtain an oily residue. This residue is dissolved in 150 ml of ethanol. To the solution, 50 ml of 5.7 N hydrogen chloride in ethyl acetate is added. The resultant solution is concentrated under reduced pressure. The crystalline residue is mixed with 50 ml of ethanol and filtered to obtain 29.0 g of the desired product. This compound is tested for NMR after it has been freed from hydrochloric acid, and it is tested for IR in its unaltered form of hydrochloride.

NMR (δ in ppm in CDCl$_3$): 1.66–2.33(6H, m), 2.6–3.2(2H, m), 3.48(2H, s), 4.0(1H, m), 4.43(2H, s), 4.80(1H, br.s) (exchangeable proton), 7.0–7.4(9H, m).

IR (KBr) $\nu_{max}^{cm-1}$: 1330, 1165 (SO$_2$) cm$^{-1}$.

REFERENCE EXAMPLE 10

4-(3,4-Dihydro-2,2-dioxo-2,1,3-benzothiadiazin-1-yl)-piperidine monohydrochloride

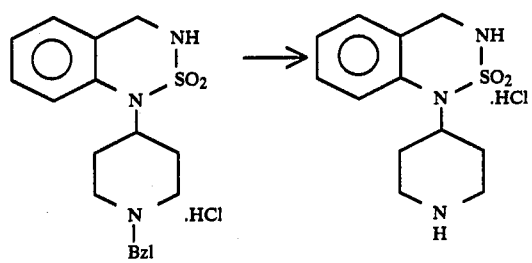

While a mixture of 16 g of 1-benzyl-4-(3,4-dihydro-2,2-dioxo-2,1,3-benzothiadiazin-1-yl)-piperidine monohydrochloride, 4 g of 10% palladium carbon, 160 ml of water and 240 ml of methanol is stirred at 40° C., hydrogen gas is blown into the mixture for 20 hours. Then, the resultant reaction mixture is freed from palladium carbon by filtration. The filtrate is concentrated to dryness to obtain 11.2 g of crude crystals of the desired product. This compound is tested for NMR after it has been freed from hydrochloric acid, and it is tested for IR in its unaltered form of hydrochloride.

NMR (δ ppm in CDCl$_3$): 1.60–3.26(8H, m), 3.70–4.26 (3H, m) (exchangeable proton 2H), 4.40(2H, s), 6.86–7.46(4H, m).

IR (KBr) $\nu_{max}^{cm-1}$: 1340, 1160 (SO$_2$) cm$^{-1}$.

What is claimed is:

1. A compound represented by the formula:

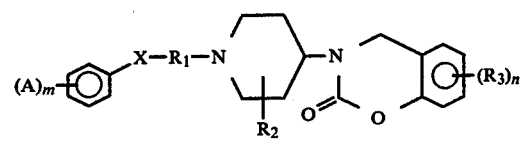

wherein A is hydroxy, halogen, lower alkyl, lower alkoxy, lower alkenyloxy, lower alkinyloxy, lower alkylthio, carboxy, lower alkoxycarbonyl, nitro, amino, lower alkylamino, lower alkanoylamino, sulfamoyl, mono- or di-lower alkylaminosulfonyl, lower alkylsulfonyl, carbamoyl, cyano or trifluoromethyl, m is 0 or an integer of 1–5, and when m is 2 or more, each A is the same group or each A is a different group or two A groups may combine to form lower alkylenedioxy; X is oxygen, sulfur, carbonyl, hydroxymethylene or methylene; $R_1$ is straight-chain alkylene having 1–4 carbon atoms with or without lower alkyl substituent(s); $R_2$ is hydrogen or lower alkyl; and $R_3$ is hydroxy, lower alkoxy, halogen, trifluoromethyl, trifluoromethoxy, trifluoromethylthio, nitro or amino, n is 0 or an integer of 1–4, and when n is 2 or more, each $R_3$ is the same group or each $R_3$ is a different group of two $R_3$ groups may combine to form lower alkylenedioxy and a pharmacologically acceptable acid addition salt thereof.

2. A compound represented by the formula:

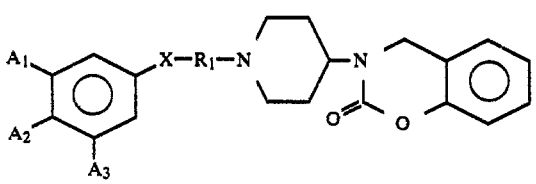

wherein $A_1$, $A_2$ and $A_3$ each represent the same group or a different group, and $A_1$, $A_2$ and $A_3$ each are hydrogen, hydroxy, halogen, lower alkyl, lower alkoxy, lower alkenyloxy, lower alkinyloxy, lower alkylthio, carboxy, lower alkoxycarbonyl, nitro, amino, lower alkylamino, lower alkanoylamino, sulfamoyl, mono- or di-lower alkylaminosulfonyl, lower alkylsulfonyl, carbamoyl, cyano or trifluoromethyl, and $A_1$ and $A_2$ or $A_2$ and $A_3$ may combine to form a lower alkylenedioxy, and X is oxygen, sulfur, carbonyl, hydroxymethylene or methylene; $R_1$ is straight-chain alkylene having 1-4 carbon atoms with or without lower alkyl substituent(s); and a pharmacologically acceptable acid addition salt thereof.

3. A compound according to claim 2, wherein at least one of $A_1$, $A_2$ and $A_3$ is lower alkoxy or halogen, or $A_1$ and $A_2$ or $A_2$ and $A_3$ combine to form lower alkylenedioxy.

4. A compound according to claim 2, wherein X is carbonyl or hydroxymethylene.

5. A compound according to claim 2, wherein $R_1$ is methylene with or without lower alkyl substituent(s).

6. A compound according to claim 1 or 2 wherein said pharmacologically acceptable acid addition salt thereof is selected from the group consisting of hydrochloride, hydrobromide, hydroiodide, nitrate, sulfate, phosphate, acetate, benzoate, maleate, fumarate, succinate, tartrate, citrate, oxalate, glyoxylate, aspartate, methanesulfonate, ethanesulfonate, propanesulfonate, methanedisulfonate, α,β-ethanedisulfonate and benzenesulfonate.

7. A hypotensive composition which comprises at least one pharmaceutically acceptable carrier, and an effective amount of a compound represented by the formula:

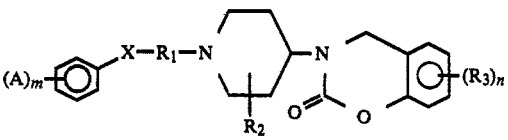

wherein A is hydroxy, halogen, lower alkyl, lower alkoxy, lower alkenyloxy, lower alkinyloxy, lower alkylthio, carboxy, lower alkoxycarbonyl, nitro, amino, lower alkylamino, lower alkanoylamino, sulfamoyl, mono- or di-lower alkylaminosulfonyl, lower alkylsulfonyl, carbamoyl, cyano or trifluoromethyl, m is 0 or an integer of 1-5, and when m is 2 or more, each A is the same group or each A is a different group or two A groups may combine to form lower alkylenedioxy; X is oxygen, sulfur, carbonyl, hydroxymethylene or methylene; $R_1$ is straight-chain alkylene having 1-4 carbon atoms with or without lower alkyl substituent(s); $R_2$ is hydrogen or lower alkyl; and $R_3$ is hydroxy, lower alkoxy, halogen, trifluoromethyl, trifluoromethoxy, trifluoromethylthio, nitro or amino, n is 0 or an integer of 1-4, and when n is 2 or more, each $R_3$ is the same group or each $R_3$ is a different group or two $R_3$ groups may combine to form lower alkylenedioxy or a pharmacologically acceptable acid addition salt thereof.

* * * * *